(12) United States Patent
Freudenthal et al.

(10) Patent No.: US 7,097,653 B2
(45) Date of Patent: Aug. 29, 2006

(54) IMPLANT FOR THE CLOSING OF DEFECT OPENINGS IN THE BODY OF A HUMAN OR ANIMAL AND A SYSTEM FOR THE PLACEMENT OF SUCH AN IMPLANT

(75) Inventors: Franz Freudenthal, Riobamba (EC); Georg Siegner, Luneburg (DE)

(73) Assignee: PFM Produkte fur die Medizin Aktiengesellschaft, Cologne (DE)

( * ) Notice: Subject to any disclaimer, the term of this patent is extended or adjusted under 35 U.S.C. 154(b) by 62 days.

(21) Appl. No.: 10/169,655

(22) PCT Filed: Jan. 3, 2001

(86) PCT No.: PCT/EP01/00012

§ 371 (c)(1),
(2), (4) Date: Nov. 5, 2002

(87) PCT Pub. No.: WO01/49185

PCT Pub. Date: Jul. 12, 2001

(65) Prior Publication Data

US 2003/0171774 A1    Sep. 11, 2003

(30) Foreign Application Priority Data

Jan. 4, 2000 (DE) ................................ 100 00 137

(51) Int. Cl.
*A61B 17/08* (2006.01)
*A61M 29/00* (2006.01)

(52) U.S. Cl. ........................ 606/213; 606/200

(58) Field of Classification Search ............ 606/213, 606/215, 216, 217, 151, 200, 198, 113; 623/1.11; 600/585

See application file for complete search history.

(56) References Cited

U.S. PATENT DOCUMENTS 5,108,406 A * 4/1992 Lee .............................. 606/113

(Continued)

FOREIGN PATENT DOCUMENTS

DE     28 22 603     3/1987

(Continued)

OTHER PUBLICATIONS

Noel L. Mills et al., "Nonoperative Closure of Left-to-Right Shunts," The Journal of Thoracic and Cardiovascular Surgery, 1976, pp. 371-378, vol. 72.

(Continued)

*Primary Examiner*—Julian W. Woo
(74) *Attorney, Agent, or Firm*—Paul A. Beck & Associates, P.C.

(57) ABSTRACT

An implant for the closing of defect openings in the body of a human or animal is proposed, with a load-bearing structure which, in a first operating state (primary form), has a great ratio of length to transverse extent along an axis (9) and, at least in a further operating state (secondary form), has a much smaller ratio of length to transverse extent along the axis (9), the load-bearing structure (1) being capable of being reversibly transformed from the secondary form into the primary form by exertion of a force against elastic material forces, the secondary form assuming approximately the form of a double disc with a proximal disc element (7) and a distal disc element (6) for receiving the surroundings of the defect opening between the disc elements, and the load-bearing structure (1) being formed essentially in one piece without joining connections, and a placement system.

30 Claims, 11 Drawing Sheets

U.S. PATENT DOCUMENTS

| | | | | |
|---|---|---|---|---|
| 5,108,420 | A | * | 4/1992 | Marks ....................... 606/213 |
| 5,192,301 | A | | 3/1993 | Kamiya et al. |
| 5,234,458 | A | | 8/1993 | Metais |
| 5,334,217 | A | | 8/1994 | Das |
| 5,425,744 | A | | 6/1995 | Fagan et al. |
| 5,433,727 | A | | 7/1995 | Sideris |
| 5,486,193 | A | | 1/1996 | Bourne et al. |
| 5,536,274 | A | | 7/1996 | Neuss |
| 5,683,411 | A | | 11/1997 | Kavteladze et al. |
| 5,709,707 | A | | 1/1998 | Lock et al. |
| 5,733,294 | A | * | 3/1998 | Forber et al. ............... 606/151 |
| 5,853,422 | A | * | 12/1998 | Huebsch et al. ............ 606/213 |
| 5,861,003 | A | * | 1/1999 | Latson et al. ............... 606/213 |
| 6,123,715 | A | * | 9/2000 | Amplatz ..................... 606/200 |
| 6,355,052 | B1 | | 3/2002 | Neuss et al. |
| 6,391,036 | B1 | * | 5/2002 | Berg et al. .................. 606/151 |
| 6,966,914 | B1 | * | 11/2005 | Abe ........................... 606/113 |

FOREIGN PATENT DOCUMENTS

| | | |
|---|---|---|
| DE | 41 04 702 | 8/1992 |
| DE | 42 22 291 | 1/1994 |
| DE | 44 10 256 | 9/1994 |
| DE | 196 04 817 | 8/1997 |
| EP | 0 474 887 | 3/1992 |
| EP | 0 545 091 | 6/1993 |
| GB | 1 509 023 | 4/1978 |
| WO | WO 93/13712 | 7/1993 |
| WO | 95/27448 | 10/1995 |
| WO | WO 96/01591 | 1/1996 |
| WO | WO 97/28744 | 8/1997 |
| WO | WO 98/02100 | 1/1998 |

OTHER PUBLICATIONS

William J. Rashkind et al., "Nonsurgical Closure of Patent Ductus Arteriosus: Clinical Application of the Rashkind PDA Occluder System," Circulation, 1987, pp. 583-592, vol. 75.

James E. Lock et al., "Transcatheter Closure of Atrial Septal Defects," Circulation, 1989, pp. 1091-1099, vol. 79.

E.B. Sideris et al., "Transvenous Atrial Septal Defect Occlusion in Piglets with a 'Buttoned' Double-Disk Device," Circulation, 1990, pp. 312-318, vol. 81.

Dusan Pavcnik et al., "Monodisk: Device for Percutaneous Transcatheter Closure of Cardiac Septal Defects," Cardio Vascular and Interventional Radiology, 1993, pp. 308-312, vol. 16.

Gladwin S. Das et al., "Experimental atrial Septal Defect Closure with a New, Transcatheter, Self-Centering Device," Circulation, 1993, pp. 1754-1764, vol. 88.

Eleftherios B. Sideris et al., "Occlusion of Large Atrial Septal Defects with a Centering Buttoned Device: Early Clinical Experience," American Heart Journal, 1996, pp. 356-359, vol. 131.

Christopher H. Pozza et al., "Transcatheter Occlusion of Patent Ductus Arteriosus Using a Newly Developed Self-Expanding Device," Investigative Radiology, 1995, pp. 104-109, vol. 30.

European Patent Office, "International Search Report from International Application Published under the Patent Cooperation Treaty," International Application No. PCT/EP97/00500.

German Patent Office, "List of References Cited in DE 196 04 817," Published Aug. 14, 1997.

European Patent Office, International Preliminary Examination Report from International Application Published Under the Patent Cooperation Treaty, International Application No. PCT/EP97/00500.

European Patent Office, "International Search Report from International Application Published Under the Patent Cooperation Treaty," International Application No. PCT/EP01/00012.

European Patent Office, "International Preliminary Examination Report from International Application Published Under the Patent Cooperation Treaty," International Application No. PCT/EP01/00012.

* cited by examiner

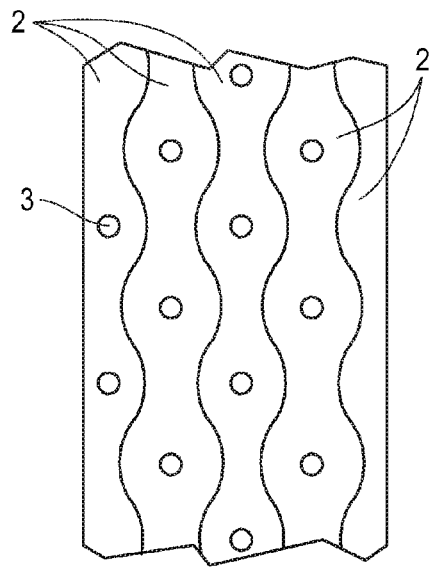
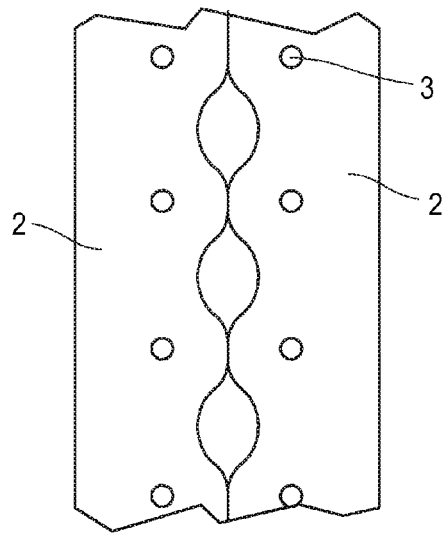
*Fig.3*  *Fig.4*
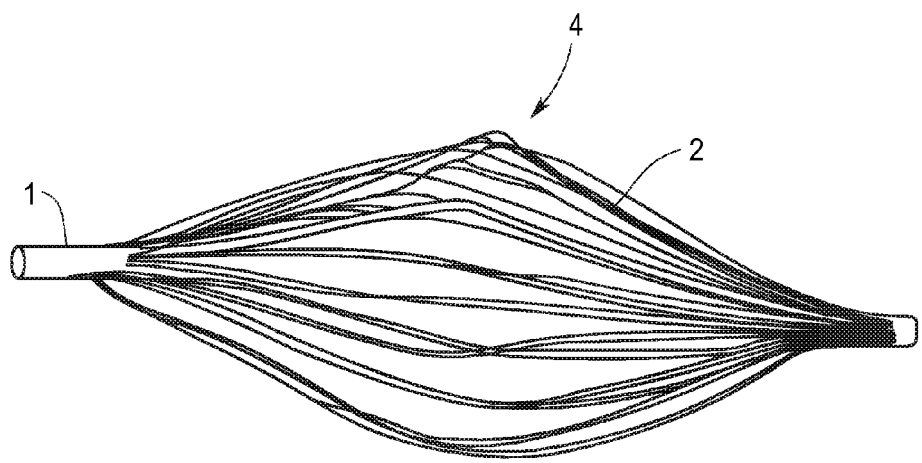
*Fig.5*

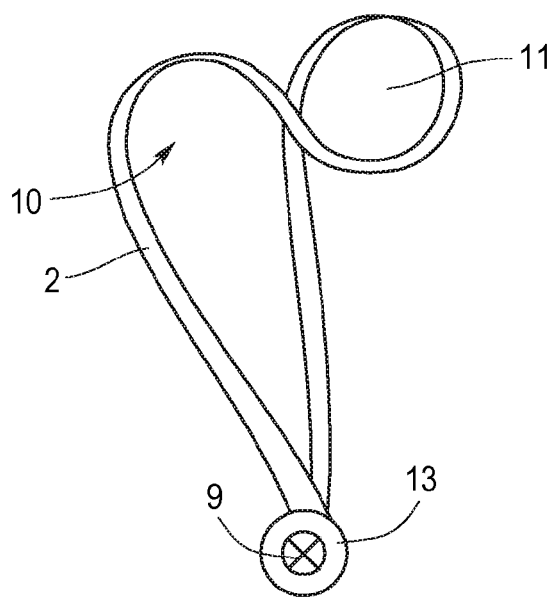
*Fig.10*
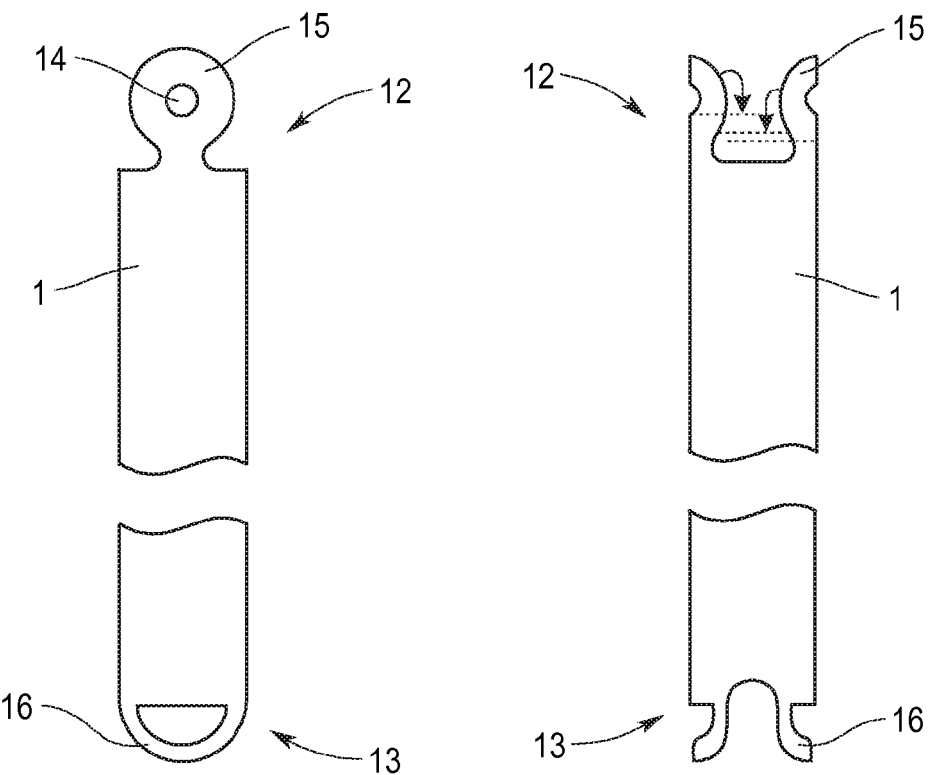
*Fig.11a*  *Fig.11b*

IMPLANT FOR THE CLOSING OF DEFECT OPENINGS IN THE BODY OF A HUMAN OR ANIMAL AND A SYSTEM FOR THE PLACEMENT OF SUCH AN IMPLANT

BACKGROUND OF THE INVENTION

1. Field of the Invention

The present invention relates to an implant for the closing of defect openings in the body of a human or animal and to a system for the placement of such an implant.

In particular in the treatment of vascular disorders, in order to reduce the risk of complications and reduce the trauma for patients caused by major operations it has been endeavoured for years to treat vascular defects by minimally invasive surgery. In such surgery, the site to be treated is not opened directly by an operation but instead instruments and implants are introduced through relatively small incisions, in particular into the abdominal cavity. In cardiology, treatment is preferably carried out by means of catheters, which are introduced into the vascular system at a suitable location, in particular via the major arteries of the leg. In this so-called interventional treatment, instruments and implants are introduced through the catheters or sheaths in order to perform the interventions.

In particular for the treatment of septal defects of the heart, interventional treatment offers enormous advantages, since it is not necessary to open the thorax and cut open the heart, which is sensitive and difficult to stop.

For this purpose, the prior art discloses a series of implants and catheter systems with which implants for the closure of defect openings can be introduced into the body and placed at the site of the defect.

2. Description of the Prior Art

An implant of the type mentioned at the beginning and a catheter system for the placement of such an implant are described in WO 97/28744. In this document there are also a large number of references to further literature and a discussion of U.S. Pat. No. 5,108,420 A, DE 42 22 291 A1, DE 28 22 603 A, U.S. Pat. No. 5,108,420 A and WO 96/01591.

Furthermore, WO 93/13712 discloses an implant for the closure of septal defects which in the implanted state assumes a double-cone or double-disc configuration, the outer structures respectively being formed by wire elements which are not directly connected to one another and are covered with fabric membranes, with the fabric membranes being sewn together in a radius corresponding to the defect to be closed. A major disadvantage of this system is that the implant constructed from a plurality of structural elements requires considerable effort for its assembly, in particular since the diameter of the sewn region has to be adapted to the diameter of the septal defect to be closed. Mass production instead of complex one-off fabrication could only be achieved if large quantities of such implants with graduated diameters of the sewn seams were produced surplus to immediate requirements and kept in stock. It goes without saying that such a course of action would not necessarily be economically advantageous in comparison with one-off assembly, since an enormous number of implants which may never be used would have to be stored at delivery depots and the like.

In WO 95/27448 there is a description of an implant which is to be used as a vein filter and for which it is also proposed that it be used as a load-bearing structure for a septal closure. In this case, a relatively elongated double cone is formed from a series of individual wires, the cones being directed towards each other in the manner of a bone in one configuration and being made to point in the same direction, similar to a fly agaric toadstool, in a further configuration.

U.S. Pat. No. 5,433,727 A discloses an implant in which a type of umbrella is placed in front of a septal defect and is secured through the defect by a counter-closure, which is essentially formed by four loops respectively produced by a wire, which unfold when ejected from a catheter and are intended to prevent the implant from slipping through to the umbrella side.

Finally, EP 0 474 887 A1 discloses an implant in which two round or otherwise polygonally shaped sealing patches, which are respectively stretched out by a peripheral compliant frame element, are connected inter alia by means of a multiplicity of threads, which have to be pulled tight through the catheter for the placement of the implant. In a further embodiment, a central snap closure is to be provided for the positional securement of the two patches. The implant described there is very difficult to place on account of the considerable effort needed for its manipulation and also requires complicated assembly which is very prone to faults.

An implant for the closure of septal defects in particular, with which quite secure placement is possible and with which erroneous seating can be corrected and, if necessary, the implant can be withdrawn again into a catheter until it is finally discharged, is described in the already mentioned WO 97/28744. The implant described there unfolds of its own accord, on account of a secondary structure impressed on it, when it is ejected from the catheter and adapts itself within broad limits to the dimensions of the defect by elastic forces. On account of the structure impressed in the superelastic material described, the parts of the implant arranged in the manner of a double disc on both sides of the septum clamp elastically against the surrounding region of the septum and in this way lead to a particularly secure seating and low leakage, the so-called residual shunt. In this case, the implant is formed by a series of wire-shaped elements, which are connected to one another by suitable joining processes, such as ultrasonic welding or brazing. Finally, the implant is also provided with a covering, which is appropriately fastened to the wire-shaped elements.

If suitable for the treatment of septal defects, all the implants described have the disadvantage that they comprise a plurality of individual parts which have to be assembled or connected to one another by joining processes. This is not a major problem for verifying the functional capability of such an implant and when small numbers are concerned, but is not very expedient for mass production, since the reliable functioning of the connecting locations has to be checked, involving considerable effort in terms of quality assurance, because of the great responsibility which the product entails, and the same applies to the other assembly steps. Voids possibly occurring during the joining processes also harbour the risk that during production they will be colonized by germs, which possibly cannot be reliably killed by sterilization and may be released after prolonged use or if fatigue ruptures occur.

SUMMARY OF THE INVENTION

The invention is therefore based on the object of providing an improved implant in comparison with the known implants, in particular with regard to economical mass production, and a placement system.

This object is achieved according to the invention by an implant for the closing of defect openings in the body of a human or animal, with a load-bearing structure which, in a first operating state (primary form), has a great ratio of length to transverse extent along an axis and, at least in a further operating state (secondary form), has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially in one piece without joining connections.

The way in which an implant is designed according to the invention not only makes it possible to combine virtually all the functional advantages of the implants known from the prior art, such as self-centring, automatic adaptation to the size of the defect to be closed, self-clamping to the surrounding tissue, fast growth with epithelial tissue due to minimal residual flow and mechanical stability, but also makes economical mass production possible by reduced effort in terms of machining, assembly and quality assurance, and last but not least a low required number of variants for children and adults. This also makes it possible to make the costs of treating otherwise life-threatening heart defects affordable even for those people who were previously excluded from enjoying the benefits of modern medicine.

The load-bearing structure being formed essentially in one piece without joining connections minimises the risk of a failure of the structure, as no connections may be subject to a failure of the same, for instance due to embrittlement of a weld connection.

In an advantageous embodiment, an implant according to the invention is characterized in that the load-bearing structure is formed by a tube slit over part of its length. This allows the one-piece structure of the load-bearing element to be favourably maintained with available production processes.

The tube preferably consists of a metallic shape-memory material, whereby an appropriate wall thickness provides good X-ray visibility, which facilitates the operation.

For good adaptation of the rigidity of the implant, it is advantageous if strips are formed along the slit part of the length along the tube, with the width of the strips varying along the slit part of the tube.

For further controlling the rigidity of parts of the implant, it is particularly expedient if strips are formed along the slit part of the length along the tube, with holes being formed in the strips, at least partly along the slit part of the tube. These holes may also serve for the fastening of one or more membranes for sealing off the defect to be closed.

If there are great changes in shape, it may be advantageous if strips are formed along the slit part of the length along the tube, with the strips arranged spirally with respect to the axis of the implant, at least over part of their length, whereby a tangential arrangement of the strips in the manner of spokes is obtained in the secondary form.

It is particularly economical from a production engineering viewpoint if strips are formed along the slit part of the length along the tube, with the mutually facing contours of respectively neighbouring strips formed in such a way as to be complementary to one another, at least along part of their length.

If offcuts are acceptable, it may also be expedient for forming a required distribution of rigidity if strips are formed along the slit part of the length along the tube, with the mutually facing contours of respectively neighbouring strips being formed in such a way as to be mirror-inverted in relation to one another, at least along part of their length.

For particularly dependable placement of the implant, it is advantageous if the load-bearing element has a variable rigidity along part of its length, the rigidity being less in particular in the region in which the proximal disc element is formed than in the region in which the distal disc element is formed. As a result, the implant can initially be inserted right through the opening and the distal disc element unfolded. Even if this involves bringing the proximal disc element partly or entirely with it into the secondary form, it is possible to draw the implant into the defect opening, since the relatively compliant proximal part easily slips through the opening, but the more rigid distal disc element offers great resistance to being inadvertently pulled through the opening.

Particularly precise distribution of rigidity can be obtained by selective superficial removal in regions where the surface of the load-bearing element is etched and/or electrochemically polished in the region of reduced rigidity.

A particularly good variation of the rigidity of the distal disc element and proximal disc element can be obtained if strips are formed along a slit part of the length along the tube, with a strip in the secondary form describing along the axis from the proximal end of the implant an arc which is open in the direction of the axis and is adjoined towards the distal end in opposed curvature by a loop.

For obtaining the desired sealing effect of the implant after implantation and little risk of forming thrombi during operation, one or more membranes may be fastened to at least some of the holes in the strips at least for covering the proximal disc element in the secondary form of the implant. For many applications it may be advantageous that said one or more membranes are formed by a stringing with metallic wire or yarn, preferably in a helix arrangement when assuming the secondary form. For filter applications a coarse stringing of nitinol wire may be suitable while a fine stringing of a polymer yarn may provide greater flow resistance.

For receiving a placement system, it is advantageous if the load-bearing element has at its proximal end and its distal end in each case at least one through-hole, which are arranged approximately in line with one another and approximately on the axis, and the hole at the distal end having a smaller diameter than the hole at the proximal end, and/or if the load-bearing element has at its proximal end at least one eyelet for the fastening of holding elements of a placement system.

It is further advantageous if the distal end and/or the proximal end of the implant are configured to allow, when implanted, proper grasping by a snare type probe for removal of the implant.

In a further advantageous embodiment, an implant according to the invention is characterized in that the load-bearing structure is formed by a tube slit over two portions of part of its length, so that an unslit portion remains approximately in the middle of the tube, and in the secondary form the proximal disc element and the distal disc element are respectively formed on one side of the unslit portion for receiving the surroundings of the defect opening between the disc elements. Preferably, the unslit portion comprises a hollow passageway in general along the axis of the tube, having a predetermined cross sectional area adapted to a desired shunt flow when implanted.

Although this dispenses with the self-centring of the implant, the formation of a solid middle piece with a relatively small diameter allows, as a special feature, the treatment of Persistent Foramen Ovale (PFO), a congenital defect of the atrium of the heart which, according to recent investigations, afflicts approximately every one in four adults to a more or less noticeable extent. With this defect, the atrial shunt of the unborn child is not completely closed but instead a kind of membrane forms, which however is not joined to the surrounding tissue on all sides. When there are sudden variations in pressure, for example during coughing, this membrane may partially open and establish a partial bypass between the lesser circulation and the greater circulation.

Thrombi possibly from the vein system may be swept away when the membrane opens, for example during coughing, into the arterial system and may cause a stroke. Previously known implants are not suitable for the treatment of PFO because of the disturbance by the membrane during placement of the implant.

A further expedient use of the implant according to the invention is possible without membrane coverage by it being used as a vascular filter. In this case, depending e.g. on the diameter of the vena cava, the formation of the secondary form is reduced, so that a low-cost and replaceable vascular filter, which can even be removed again, is obtained for capturing thrombi, while utilizing all the remaining advantages of the implant and the placement system according to the invention.

Another expedient use of a device and optionally a placement system according to the invention is possible for the removal of stones or other agglomerates or foreign bodies from a human or animal body.

Furthermore, this object is achieved according to the invention by a placement system, in particular for an implant described above, with a stretching element and at least one, preferably two, holding wires, the stretching element serving for interacting with a distal end of an implant and the holding wire or wires serving for interacting with a proximal end of an implant, the implant being capable of being transformed from a primary form into a secondary form and vice versa by relative movement of the holding wires in relation to the stretching element.

The placement system according to the invention allows the implantation of, in particular, an implant according to the invention to be significantly simplified and made more dependable by simple and reliable means, by the implant being discharged completely from the introducing catheter and able just to "float" on the stretching element at the placed site, so that checking for a satisfactory seating and adequate sealing effect when the heart is working, and being moved correspondingly vigorously, can be performed, with the possibility of replacement if need be.

In a particularly advantageous configuration, in a placement system according to the invention the stretching element is formed by a stretching cannula, and furthermore the placement system has a guiding wire led through the stretching cannula, and at least one, preferably two, holding wires, with the implant being capable of being transformed from a primary form into a secondary form and vice versa by relative movement of the holding wires in relation to the stretching cannula along the guiding wire. This makes it possible initially to lay the soft guiding wire through the body, including the defect opening to be closed, and subsequently advance the implant together with the catheter and the stretching cannula blindly and dependably to the defect opening, whereby the success rate is increased and the duration of an operation is significantly reduced. What is more, lower exposure of the patient to X-ray radiation can be achieved.

For particularly great dependability in the implantation, it is advantageous if the stretching element is intended to interact with a loss-preventing means provided at the distal end of an implant, preventing unintentional separation of the implant from the stretching element.

Another suitable embodiment of a placement system according to the invention has a stretching element and at least one holding wire, the stretching element serving for interacting with an end of an implant, the implant being capable of being transformed from a primary form into a secondary form and vice versa, and which furthermore has one or more guiding wires led in general through the implant and through a loop formed in the holding wire, wherein at least one of the guiding wires is led over a part of the length of the implant over the outer circumference of the same and the holding wire or wires serving for interacting with at least one of the guiding wires so that the implant is secured to the placement system unless the guiding wires or the holding wire or wires are removed, preventing unintentional separation of the implant from the placement system.

For operating through small vessel, e.g. of a child, the placement may be characterized in that the stretching element is formed by a section of a guiding wire having a larger cross sectional dimension than the remainder of the guiding wire.

BRIEF DESCRIPTION OF THE DRAWINGS

The invention is to be described in more detail below on the basis of exemplary embodiments represented in the attached drawings, in which:

FIG. 3 shows a schematic developed projection of a portion of a tube according to FIG. 2 for representing the arrangement of the cuts;

FIG. 4 shows a schematic developed projection of a portion of a tube according to FIG. 2 with a representation of another arrangement of the cuts;

FIG. 5 shows a tube according to FIG. 2, compressed after cutting;

FIG. 10 shows a schematic view of an individual strip of a particularly preferred embodiment of an implant according to the invention;

FIGS. 11a,b show ends of an implant according to the invention during production;

DESCRIPTION OF PREFERRED EMBODIMENTS OF THE INVENTION

Figure 1:
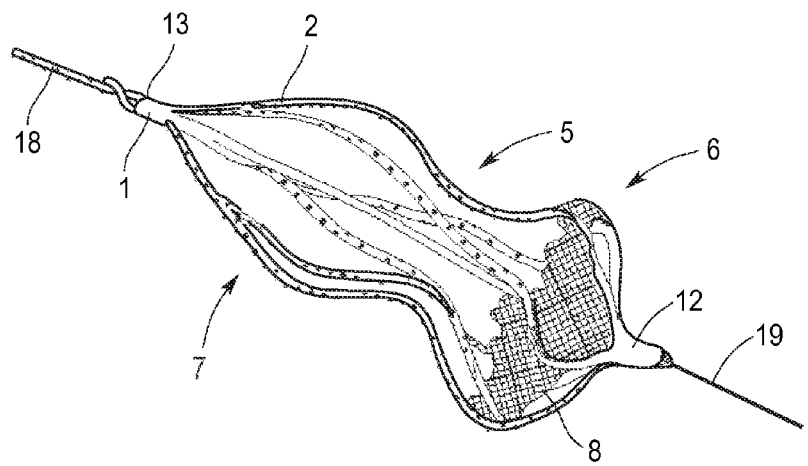
FIG. 1 shows an implant according to the invention in a perspective view, partly unfolded, with elements of a placement system according to the invention.
Figure 2:
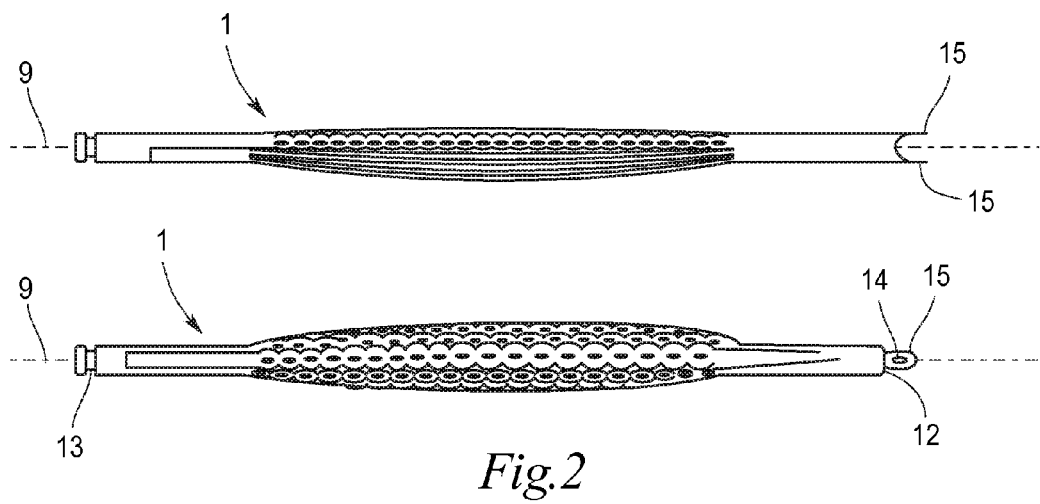
FIG. 2 shows two tubes with cuts for the forming of implants according to the invention.

Represented in a perspective view in FIG. 1 is an implant according to the invention, which has partly unfolded from its primary form into the secondary form, together with elements of a placement system according to the invention. The configuration represented in FIG. 1 is typically obtained during the placement of the implant.

The load-bearing structure of an implant according to the invention, represented in FIG. 1, is expediently produced from a tube 1 made of nitinol. Nitinol is a nickel-titanium alloy which has not only superelasticity but also the property of shape memory and is therefore particularly suited for this application. By fine laser-beam cutting, the tube 1 is slit in such a way that a number of strips 2 form. The slitting of course only takes place over part of the length of the tube 1. Furthermore, holes 3 can also be cut into the strips 2 in the same way, in order to obtain the desired distribution of rigidity and to allow one or more membranes to be fitted later. The holes may be of any expedient shape and size, for example also elliptically shaped.

Although the use of slit nitinol tubes for producing an implant according to the invention does not necessarily conform to the view in the literature of using as little material as possible, the corresponding amount of material provides good X-ray visibility and consequently dependable and quick implantation by the operating surgeon. Furthermore, adequate mechanical stability is required in order for it to withstand permanently the difference in pressure between the two ventricles of the heart of typically 100 mbar without deforming to such an extent that there is the risk of it slipping out. Further, the material of the tube may also be varied and adapted to the use of NMR control during operation instead of X-rays.

During the laser-beam cutting of such a tube 1, for example made of nitinol, it must be ensured by corresponding selection of the parameters that only the intended side of the tube is cut through, but the opposite inside wall of the tube is not damaged. By using a pulsed cutting laser, this can take place for example by reducing the pulse energy while increasing the pulse frequency and/or reducing the cutting rate.

FIG. 3 shows in a schematic developed projection of a tube a sectional profile with complementary edges of the strips, which is optimal with regard to production costs, since no offcuts are created and minimal cutting distances are necessary; the rigidity can be adapted by means of the shape, distribution and size of the holes.

FIG. 4 shows in a schematic developed projection of a portion of the tube a mirror-inverted arrangement of the edges of the strips. Although this produces a region with offcuts, greater rigidity can be obtained.

Figure 6:
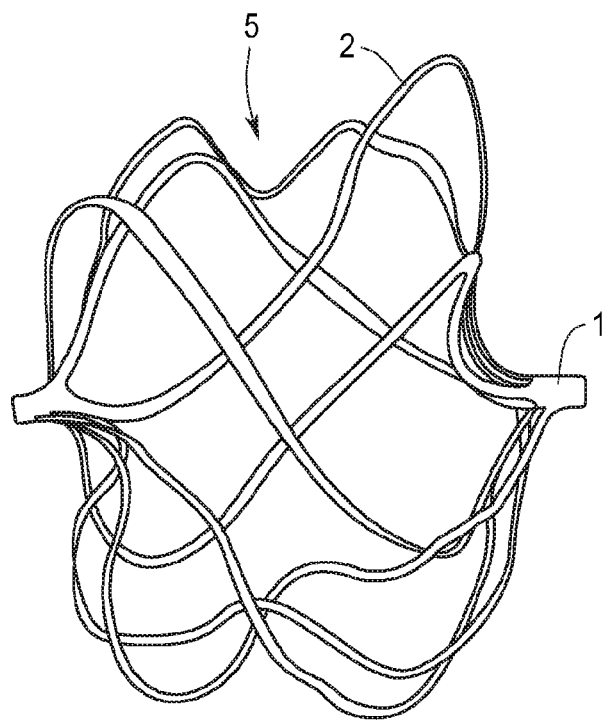
FIG. 6 shows a tube according to FIG. 5, turned further.

After the cutting, the tube 1 is compressed, as can be seen in FIG. 5. As a result, the strips 2 form a bulge 4. By turning the distal end 12 and the proximal end 13, an umbrella of a large diameter is produced. By further turning, this umbrella is constricted in the middle 5, so that a distal disc element 6 and a proximal disc element 7 form (FIG. 6).

Figure 7:
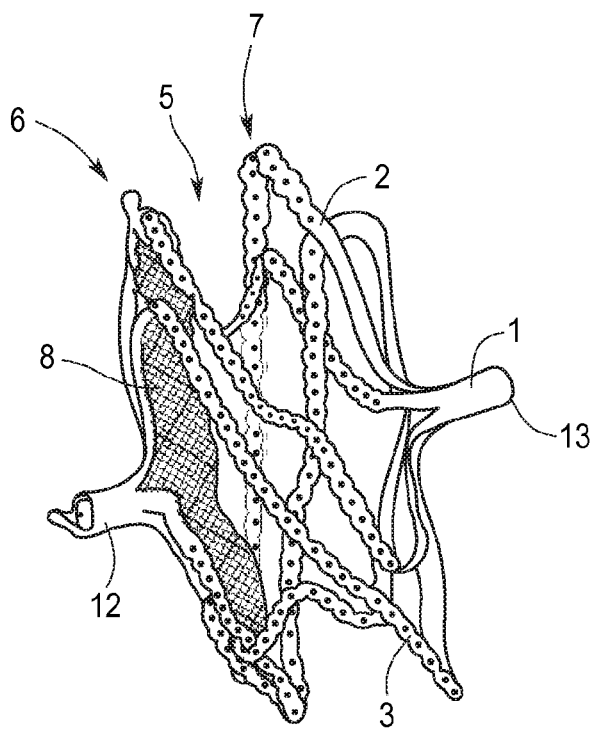
FIG. 7 shows an implant according to the invention with a membrane in a perspective view, virtually transformed into the secondary form.
Figure 8:
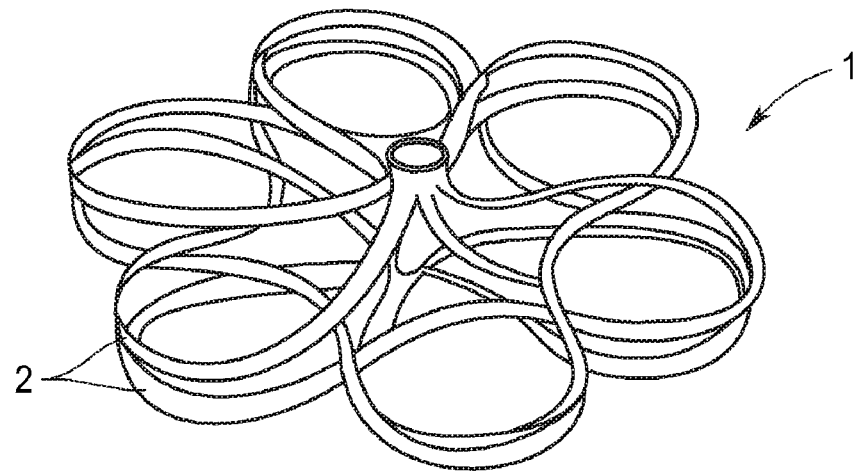
FIG. 8 shows an implant according to the invention after the impressing of the secondary form, in a perspective view.

By annealing at an appropriate temperature in a mould, the secondary form, as perspectively represented for example in FIG. 8, is impressed into the load-bearing structure. With corresponding coverage with a membrane 8, the implant can be completed (FIG. 7). In this case, it is also possible for a plurality of membranes 8 to be used, depending on the required sealing effect, since these membranes generally comprise a netting-like structure. At the same time, the membranes 8 may also be provided on different sides of the implant or envelop the implant like a pulled-over sock, with appropriate openings for a placement system.

It is not required that the membrane 8 provide for a hermetically sealing when implanted in the defect opening, but the provision of a suitable resistance against flow through the implant will do.

Suitable materials for the membranes 8 include, but not limited to, biocompatible grade PET yarn or fabric (e.g. Dacron®), PTFE (polytetraflourethylene), polyethylene (PE), and biocompatible grade polyurethanes. The membranes 8 may be fixed to the strips 2 by way of adhesive, by sewingas well as by welding of the membrane material through the holes 3 or to an auxiliary material, preferably by ultra sonic welding.

Figure 9A:
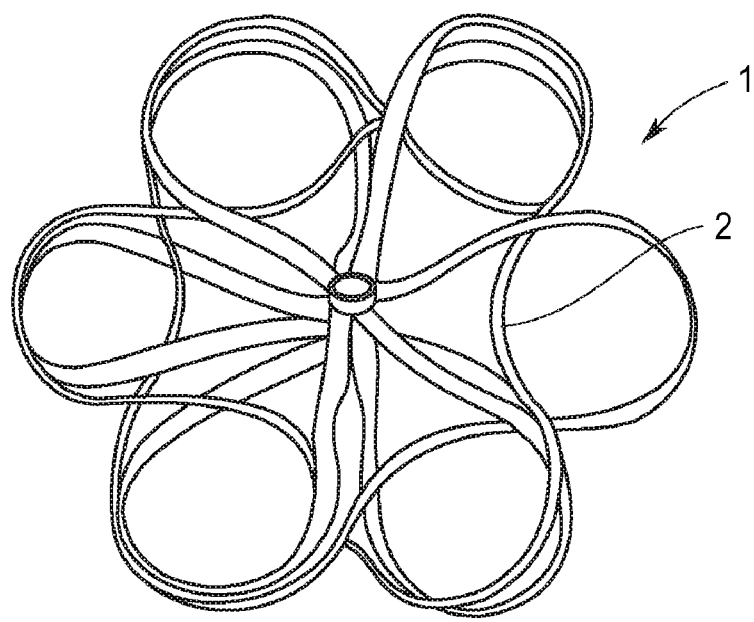
FIGS. 9a–c show further implants according to the invention after the impressing of the secondary form, in a plan view.
Figure 9B:
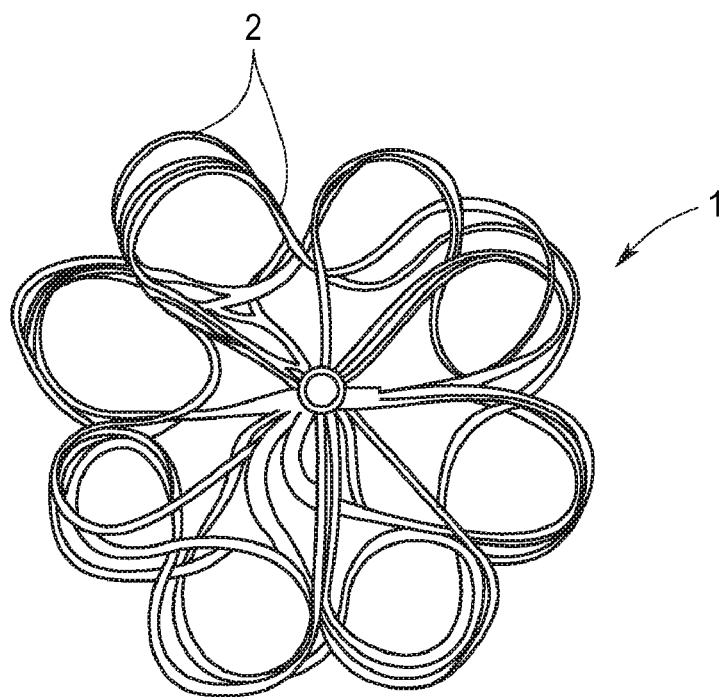
Figure 9C:
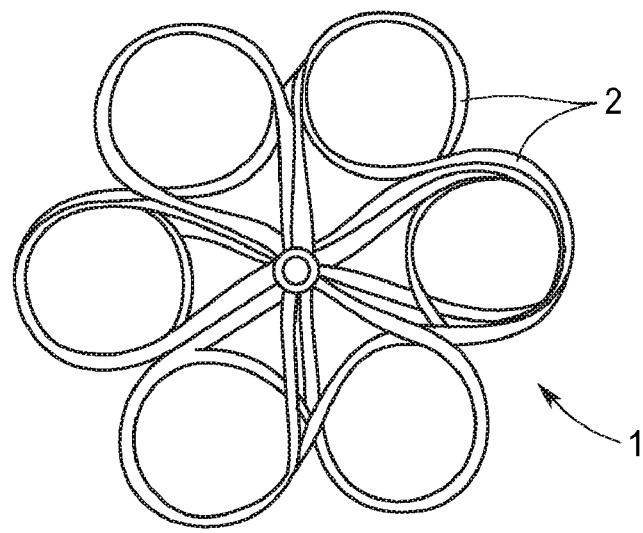

Represented in FIGS. 9a to 9c are further embodiments of the secondary form of load-bearing structures of implants according to the invention, which are attributable to different numbers of strips 2 and differently impressed shaping.

Schematically represented in FIG. 10 is a particularly preferred shaping of a strip 2, looking along the longitudinal axis 9 of the tube 1. A particularly good variation of the rigidity of the distal disc element and proximal disc element is obtained in this way, since the strip 2 in the secondary form describes along the axis 9 from the proximal end of the implant an arc 10 which is open in the direction of the axis and adjoined towards the distal end in opposed curvature by a loop 11.

The shape of the strips 2, but also selective material removal on parts of the strips 2, allow a desired distribution of rigidity to be set, providing a form which can be implanted more easily, in which the proximal disc element 7 is made softer than the distal disc element 6 (see FIG. 1).

Figure 12:
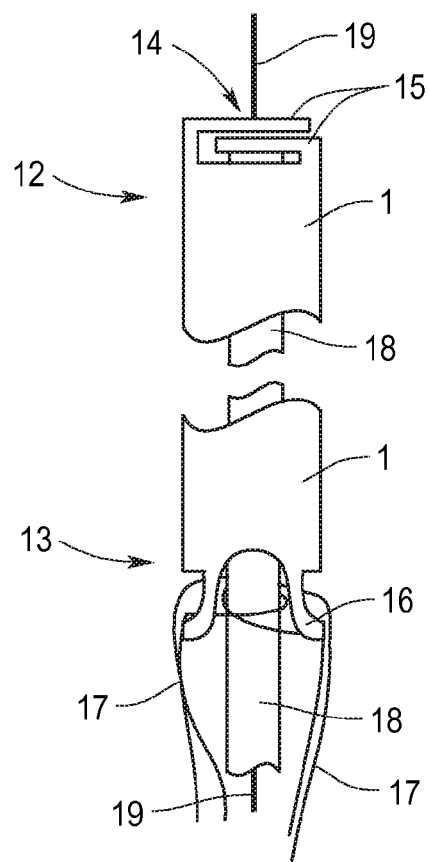
FIG. 12 shows ends of an implant according to the invention with elements of a placement system according to the invention.

An advantageous formation of the distal end 12 and proximal end 13 can be seen in FIGS. 11a and 11b. In this case, one or two lugs 15 provided with a hole 14 are produced during the cutting and are bent together before the annealing (FIG. 11b), so that a small hole is obtained along the axis 9. Formed onto the proximal end 13 are two eyelets 16, which can receive flexible holding wires 17 of a placement system according to the invention (FIG. 12).

At the same time, the distal end 12, closed by the lugs 15, forms an abutment for a stretching cannula 18, whereby the implant can be transformed counter to the elastic forces of the load-bearing structure with the aid of the holding wires 17 between the primary form, in which it virtually assumes the form of the tube 1 after cutting, and the secondary form (cf. intermediate position in FIG. 1). In the distal end 12 of the implant, a positive or non-positive securement, known per se, against inadvertent stripping off of the stretching cannula 18 may also be provided.

This allows the implant to be stretched well, guided through and out of the catheter and in particular replaced if need be outside the relatively rigid catheter. It is particularly advantageous here that the implant and the parts of the placement system in this case follow the movements of the treated defect by "floating" (in particular in the case of the beating heart). This is achieved due to the angular flexibility of the arrangement which provides no or little force on the implant although the axis of the catheter in most deviates from being perpendicular to the plane of the defect to be closed. The "floating" further allows discharging of the implant with significantly minor jolt than known from the prior art. Consequently, increased immunity to incidents occurring during such operations is ensured.

Also expediently used is a relatively soft guiding wire 19, which is led through the stretching cannula 18 and the hole 14 in the distal end 12 of the tube 1 and which may have a bent distal end formed as a pig tail, and, as a result, can initially be laid without the risk of perforations through a rigid catheter through the defect opening. The catheter with the implant can then be advanced along the guiding wire 19 blindly to all intents and purposes to the implantation site. As a result, less intensive X-ray irradiation, with its disadvantageous effects, is also required. Instead of a stretching cannula 18, a wire tapering conically in the distal direction may also be used if a guiding wire 19 is not possible or expedient.

Figure 13:
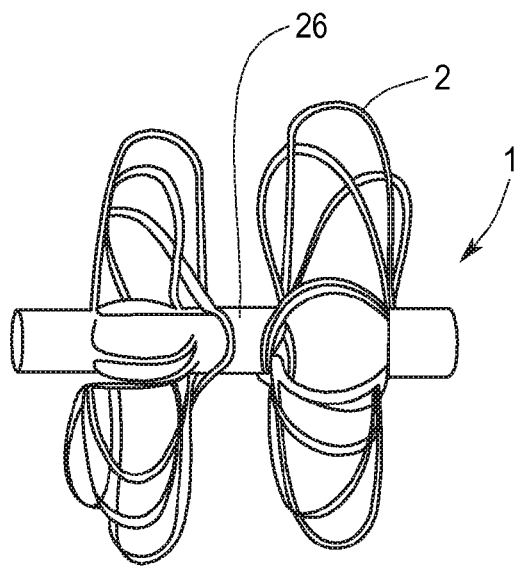
FIG. 13 shows another embodiment of an implant, for the treatment of PFO, according to the invention after the impressing of the secondary form, in a side view.

In a further advantageous embodiment, as schematically shown in FIG. 13, the load-bearing structure in an implant according to the invention is formed by a tube slit over two portions of part of its length, so that an unslit portion 26 remains approximately in the middle of the tube 1, and in the secondary form the proximal disc element and the distal disc element are respectively formed on one side of the unslit portion 26 for receiving the surroundings of the defect opening between the disc elements.

Although this dispenses with the self-centring of the implant, the formation of a solid middle piece 26 with a relatively small diameter allows, as a special feature, the treatment of Persistent Foramen Ovale (PFO), a congenital defect of the atrium of the heart which, according to recent investigations, afflicts approximately every one in four adults to a more or less noticeable extent. With this defect, the atrial shunt of the unborn child is not completely closed but instead a kind of membrane forms, which however is not joined to the surrounding tissue on all sides. When there are sudden variations in pressure, for example during coughing, this membrane may partially open and establish a partial bypass between the lesser circulation and the greater circulation.

Thrombi possibly from the vein system may be swept away when the membrane opens, for example during coughing, into the arterial system and may cause a stroke. Previously known implants are not suitable for the treatment of PFO because of the disturbance by the membrane during placement of the implant.

Such an embodiment of the invention, as shown in FIG. 13, further provides the advantage of a tract for re-drainage by forming a hollow passageway through the tube like middle piece 26 of the implant. Preferably, the unslit portion 26 comprises a hollow passageway in general along the axis 9 of the tube 1, having a predetermined cross sectional area allowing a desired shunt flow when implanted.

The distal and proximal disk elements formed with this embodiment may have different diameters each for a proper fit within the PFO.

Figure 14A:
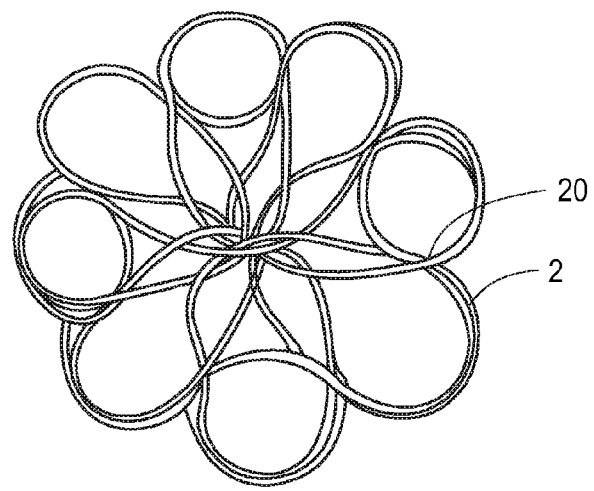
FIGS. 14a and b show a further embodiment of an implant according to the invention after the impressing of the secondary form, in a front view and a side view in a transitional state between primary and secondary forms of the implant.

FIGS. 14a and b shows a further embodiment of an implant according to the invention after the impressing of the secondary form, in a front view and a side view in a transitional state between primary and secondary forms of the implant. This embodiment is characterized by junctions 20 between adjacent strips 2 providing improved mechanical stability in the secondary form of the implant for forming large disk elements, exceeding about 40 mm in diameter.

Figure 15A:
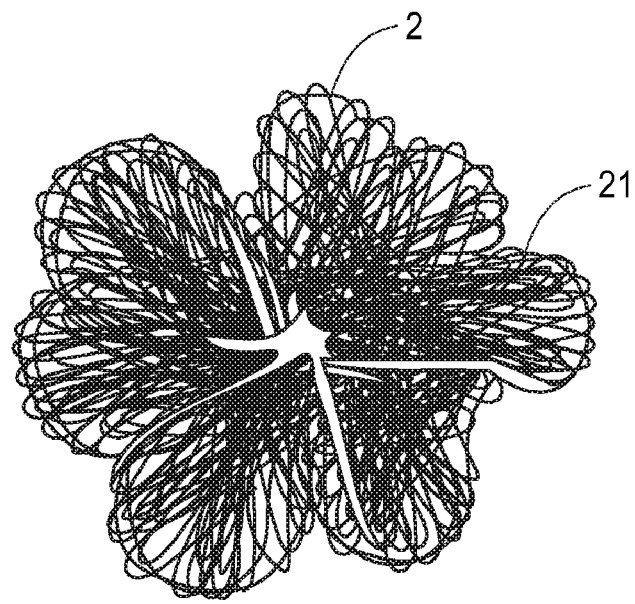
FIGS. 15a and b show another implant according to the invention after the impressing of the secondary form wherein the membrane is replaced by a stringing, in a perspective view, and in a transitional state between primary and secondary forms of the implant.
Figure 15B:
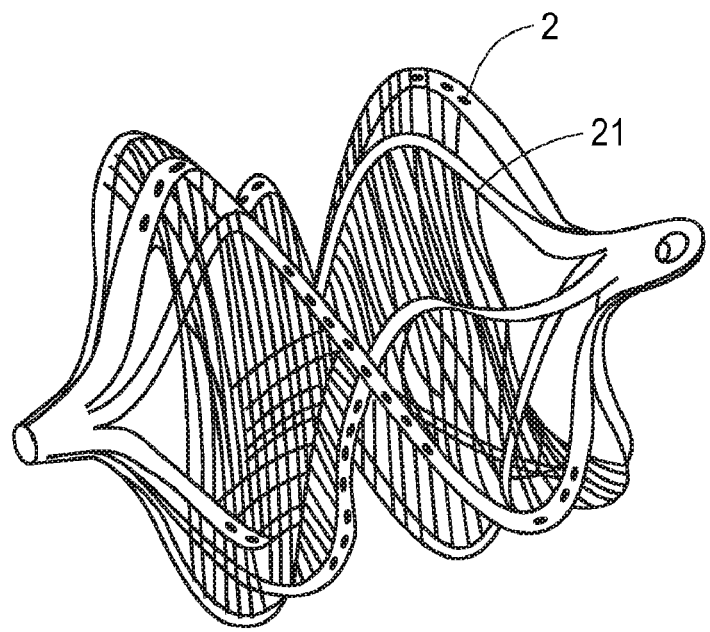

FIGS. 15a and b show another implant according to the invention after the impressing of the secondary form wherein the membrane is replaced by a stringing 21 between opposing strips 2, in particular having a helical shape in the secondary form, each. It has been found that a stringing 21 instead of a sealed membrane provides enough flow resistance to serve as a suitable defect closure, having the advantage of requiring less space in diameter when in the primary form, and thus, being easier to implant into a small child. The stringing 21 may be made from nitinol wire and will be covered by human or animal tissue within approx. 3 months time. The stringing may be made also by nitinol wire for filter applications of the implant.

Figure 16A:
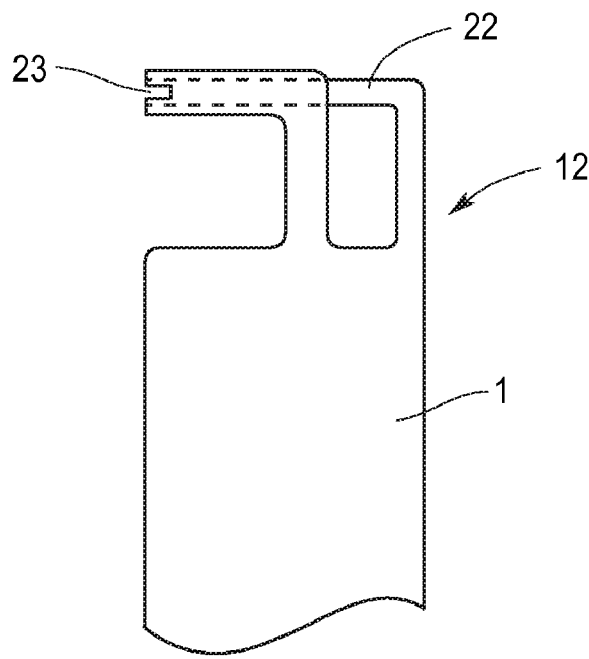
FIGS. 16a and b show a further embodiment of a distal end of an implant according to the invention, in side and perspective views.
Figure 16B:
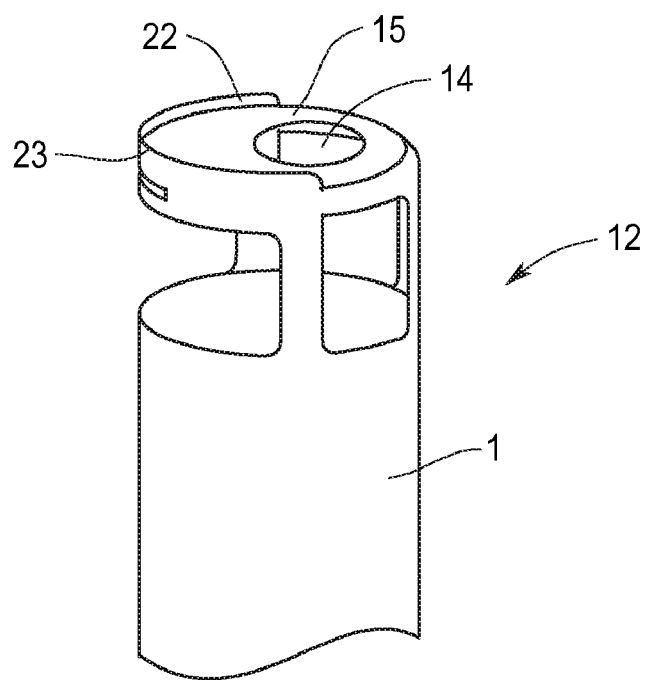

FIGS. 16a and b show a further embodiment of a distal end 12 of an implant according to the invention in side and perspective views. This embodiment has a ring like structure 22 made during cutting the nitinol tube 1 having a slit 23, and only one lug 15 is formed during cutting provided with a hole 14 and is bent towards the ring like structure 22 until the lug 15 rests within the slit 23, before the annealing, so that a small hole 14 is obtained along the axis 9.

Figure 17A:
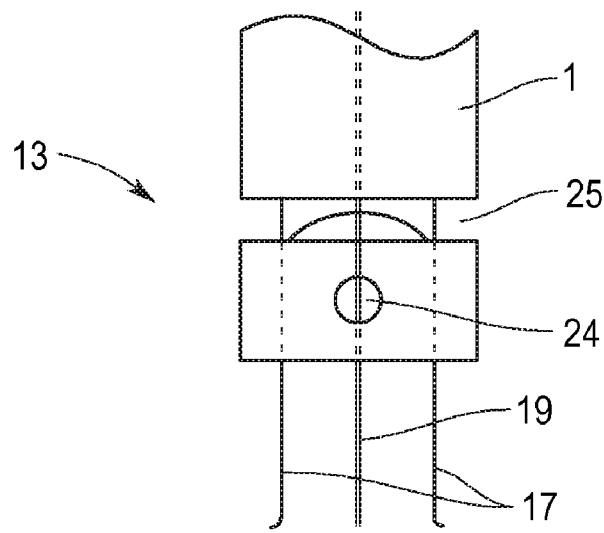
FIGS. 17a and b show a further proximal end of an implant according to the invention with elements of a placement system according to the invention.
Figure 17B:
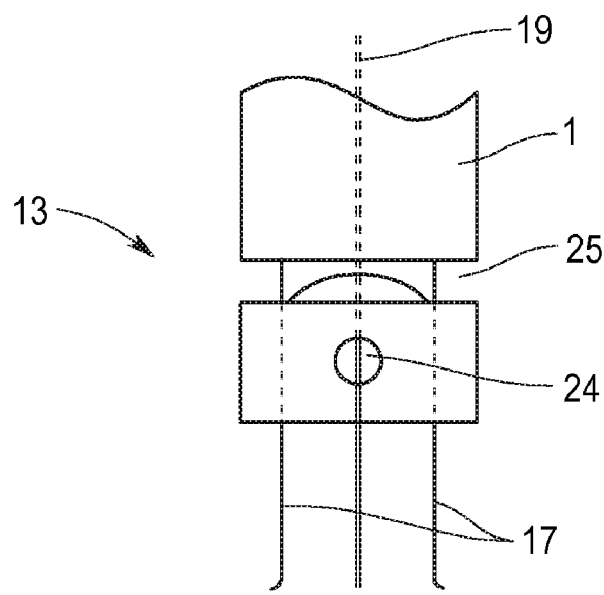

FIGS. 17a and 17b show a further proximal end of an implant according to the invention with elements of a placement system according to the invention. A guiding wire 19 led in general through the implant and through a loop formed in the holding wire 17, wherein the guiding wire 19 is led over a part of the length of the implant over the outer circumference of the same. FIGS. 17a and b show alternative configurations how the guiding wire 19 is led. In this embodiments a part of the circumference of the tube 1 at the proximal end 13 of the implant has a hole 24 and another part 25 is cut away to form a passageway for both the guiding wire 19 and the holding wire or wires 17 serving for interacting with the guiding wire 19 so that the implant is secured to the placement system unless the guiding wire 19 or the holding wire or wires 17 are removed, preventing unintentional separation of the implant from the placement system. Preferably, the stretching element is formed by a section of the guiding wire 19 having a larger cross sectional dimension than the remainder of the guiding wire 19, for instance by way of a conical shape of the guiding wire 19. The shape of the proximal end 13 further allows griping of the implant by a snare type probe which allows easy manipulation if the implant is to be replaced or removed after implantation has been completed.

Alternatively (not shown) the placement system may have for instance three guiding wires 19 led in general through the implant and at least one guiding wire 19 is led through a loop formed in the holding wire 17, wherein at least one of the guiding wires 19 is led over a part of the length while the stretching element 18 is formed by a section of a guiding wire 19 having a larger cross sectional dimension than the remainder of the guiding wire 19, and which is preferably led directly through the interior of the implant.

Not represented in the figures are further expedient embodiments of the invention.

A further expedient use of the implant according to the invention is possible without membrane coverage by it being used as a vascular filter. In this case, depending e.g. on the diameter of the vena cava, the formation of the secondary form is reduced, so that a low-cost and replaceable vascular filter is obtained for capturing thrombi, while utilizing all the remaining advantages of the implant and the placement system according to the invention. If the placement system according to the invention is used and is not separated from the implant, for example during an operation, such a vascular filter can even be removed again.

Figure 14B:
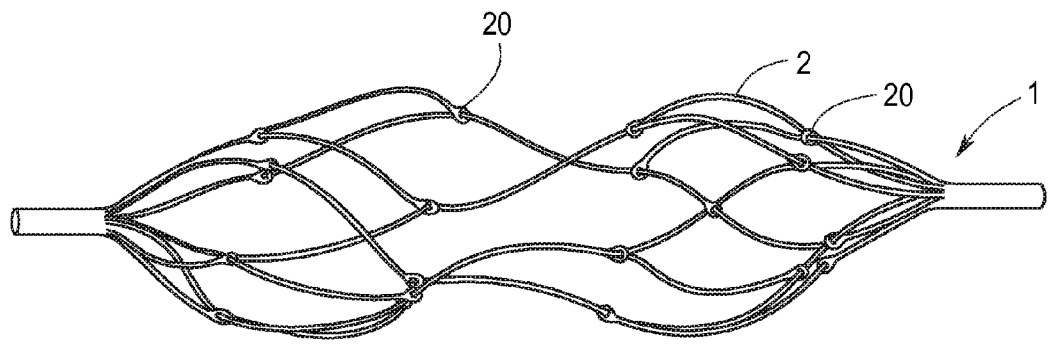

A further expedient use of a device and optionally a placement system according to the invention is possible for removal of stones or other agglomerates or foreign bodies from a human or animal body, preferably when in an intermediate configuration as shown in FIGS. 1 and 14b.

The invention claimed is:

1. An implant for the closing of defect openings in the body of a human or animal comprising a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially in one piece without joining connections by a tube slit over part of its length including the middle of the tube.

2. An implant as recited in claim 1 wherein the tube consists of a metallic shape-memory material.

3. An implant for the closing of defect openings in the body of a human or animal comprising a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially in one piece without joining connections by a tube slit over part of its length wherein strips are formed along the slit part of the length along the tube, with the width of the strips varying along the slit part of the tube.

4. An implant for the closing of defect openings in the body of a human or animal comprising a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially in one piece without joining connections by a tube slit over part of its length wherein strips are formed along the slit part of the length along the tube, with holes being formed in the strips, at least partly along the slit part of the tube.

5. An implant as recited in claim 4 wherein one or more membranes are fastened to at least some of the holes in the strips at least for covering the proximal disc element in the secondary form of the implant.

6. An implant as recited in claim 5 wherein said one or more membranes are formed by a stringing of metallic wire or yarn, and when assuming the secondary form in a helix arrangement.

7. An implant for the closing of defect openings in the body of a human or animal comprising a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially in one piece without joining connections by a tube slit over part of its length wherein strips are formed along the slit part of the length along the tube, with the ships arranged spirally with respect to the axis of the implant, at least over part of their length.

8. An implant for the closing of defect openings in the body of a human or animal comprising a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially in one piece without joining connections by a tube slit over part of its length wherein strips are formed between curved contoured slits along part of the length of the tube.

9. An implant as recited in claim 8 wherein mutually facing curved contours of respectively neighbouring strips are formed in such a way as to be mirror-inverted in relation to one another, at least along part of their length.

10. An implant as recited in claim 8 wherein mutually facing curved contours of respectively neighboring strips formed in such a way as to be complementary to one another, at least along part of their length.

11. An implant for the closing of defect openings in the body of a human or animal comprising a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially in one piece without joining connections wherein the load-bearing structure has a variable rigidity along part of its length, the rigidity being less in particular in the proximal disc element is formed than in the region in which the distal disc element is formed.

12. An implant as recited in claim 11 wherein in the surface of the load-bearing structure is etched and/or electrochemically polished in the region of reduced rigidity.

13. An implant as recited in claim 11 wherein strips are formed along a slit part of the length along the tube with a strip in the secondary form describing along the axis from the proximal end of the implant an arc which is open in the direction of the axis and is adjoined towards the distal end in opposed curvature by a loop.

14. An implant for the closing of defect openings in the body of a human or animal comprising a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially in one piece without joining connections wherein strips are formed along a slit part of the length along the tube with a strip in the secondary form describing along the axis from the proximal end of the implant an arc which is open in the direction of the axis and is adjoined towards the distal end in opposed curvature by a loop.

15. An implant for the closing of defect openings in the body of a human or animal comprising a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially in one piece without joining connections wherein the load-bearing structure has at its proximal end and its distal cad in each case at least one through-hole, which are arranged approximately in line with one another and approximately on the axis, and the hole at the distal end having a smaller diameter than the hole at the proximal end.

16. An implant according to claim 15 wherein the distal end and/or the proximal end of the implant are configured to allow, when implanted, proper grasping by a snare type probe for removal of the implant.

17. An implant for the closing of defect openings in the body of a human or animal comprising a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially from a one piece structure without joining connections wherein the load-bearing structure has at its proximal end at least one eyelet for the fastening of holding elements of a placement system.

18. An implant for the closing of defect openings in the body of a human or animal comprising a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially in one piece without joining connections including a placement system having a stretching element and a holding wire, the stretching element serving for interacting with a distal end of an implant and the holding wire serving for interacting with a proximal end of an implant, the implant being capable of being transformed from a primary form into a secondary form and vice versa by relative movement of the holding wire in relation to the stretching element, while the stretching element interacts with the distal end of the implant.

19. An implant as recited in claim 18 wherein the stretching element is formed by a stretching cannula, and which furthermore has a guiding wire led through the stretching cannula, and a holding wire, with the implant being capable of being transformed from a primary form into a secondary form and vice versa by relative movement of the holding wire in relation to the stretching cannula along the guiding wire.

20. An implant as recited in claim 18 wherein the stretching element is intended to interact with a loss-preventing means provided at the distal end of an implant, preventing unintentional separation of the implant from the stretching element.

21. An implant according to claim 18 wherein the stretching element is formed by a section of a guiding wire having a larger cross sectional dimension than the remainder of the guiding wire.

22. An implant for the closing of defect openings in the body of a human or animal comprising a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of the defect opening between the disc elements, and the load-bearing structure being formed essentially in one piece without joining connections including a placement system having a stretching element and at least one holding wire, the stretching element serving for interacting with an end of an implant, the implant being capable of being transformed from a primary form into a secondary form and vice versa, and which furthermore has at least one guiding wire led in general through the implant and the guiding wire is led through a loop formed in the holding wire, wherein the guiding wire is led over a part of the length of the implant over the outer circumference of the same and the holding wire serving for interacting with the guiding wire so that the implant is secured to the placement system unless the guiding wire or the holding wire is removed, preventing unintentional separation of the implant from the placement system.

23. A placement system for an implant with a distal end and a proximal end comprising:
   (a) a stretching element for interacting with the distal end of the implant; and
   (b) a holding wire for interacting with the proximal end of the implant whereby relative movement of the holding wire in relation to the stretching element causes the implant to transform from a primary form to a secondary form and then reverse from a secondary form to the primary form, wherein the stretching element is a stretching cannula and has a guide wire led through the stretching cannula.

24. A placement system for an implant as recited in claim 23 wherein the stretching element interacts with a loss preventing means for preventing unintentional separation of the implant, the loss preventing means is provided at the distal end of an implant.

25. A placement system for an implant as recited in claim 23 wherein the stretching element is formed by a section of a guiding wire having a larger cross sectional dimension than the remainder of the guiding wire.

26. A placement system for an implant that is capable of being transformed from a primary form into a secondary form and reversing from a secondary form into a primary form comprising:
   (a) a stretching element configured for interacting with an end of an implant;
   (b) a holding wire having a loop configured for interacting with another end of the implant; and
   (c) a guiding wire through the loop in the holding wire and extending from the stretching element, wherein the stretching element is formed by a section of the guiding wire having a larger cross-sectional dimension than the remainder of the guiding wire.

27. A method for using an implant as a vascular filter comprising:
   (a) providing an implant having a load-bearing structure which, in a primary form, has a great ratio of length to transverse extent along an axis and, in a secondary form, has a much smaller ratio of length to transverse extent along the axis, the load-bearing structure being capable of being reversibly transformed from the secondary form into the primary form by exertion of a force against elastic material forces, the secondary form assuming approximately the form of a double disc with a proximal disc element and a distal disc element for receiving the surroundings of a defect opening between the disc elements, and the load-bearing structure being formed essentially from a one piece structure without joining connections;
   (b) inserting the implant into a vascular vessel; and
   (c) forming an elongated net with the implant to capture particles.

28. A method as recited in claim 27 wherein the load-bearing element has at its proximal end and its distal end a through-hole, in which each hole is arranged approximately in line wit the other through hole and approximately on the axis, and the hole at the distal end having a smaller diameter than the hole at the proximal end.

29. A vascular filter comprising a load-bearing structure which, in a primary form, has a great ratio of length to transverse extent along an axis and, in a secondary form, has a much nailer ratio of length to transverse extent along the axis, the load-bearing structure being capable of being reversibly transformed from the secondary form into the primary form by exertion of a force against elastic material forces, the secondary form assuming approximately the form of double discs with a proximal disc element and a distal disc element for receiving the surroundings of a defect opening between the disc elements, and the load-bearing structure being formed essentially from a one piece structure without joining connections, wherein the load-bearing structure has at its proximal end and its distal end in each case at least one through-hole, which are arranged approximately in line with one another and approximately on the axis, and the hole at the distal end having a smaller diameter than the hole at the proximal end.

30. A vascular filter as recited in claim 29 wherein the diameter of the secondary form is limited by the diameter of a vascular vessel.

* * * * *

UNITED STATES PATENT AND TRADEMARK OFFICE
CERTIFICATE OF CORRECTION

| | |
|---|---|
| PATENT NO. | : 7,097,653 B2 |
| APPLICATION NO. | : 10/169655 |
| DATED | : August 29, 2006 |
| INVENTOR(S) | : Franz Freudenthal and Georg Siegner |

Page 1 of 1

It is certified that error appears in the above-identified patent and that said Letters Patent is hereby corrected as shown below:

On The Title Page, Item 30 The Foreign Application Priority Data
cancel "Jan. 4, 2000   (DE)…………..100 00 137" and insert --Jan. 4, 2000 (DE)…………..100 00 137.8--

Column 12, Line 27
cancel "ships" and insert --strips--

Column 13, Line 47
cancel "cad" and insert --end--

Column 14, Line 15 cancel
"clement" and insert --element--

Column 16, Line 18
cancel "wit" and insert --with--.

Signed and Sealed this

First Day of May, 2007

JON W. DUDAS
*Director of the United States Patent and Trademark Office*